United States Patent

Sato et al.

[11] Patent Number: 5,545,666
[45] Date of Patent: Aug. 13, 1996

[54] PROSTAGLANDIN DERIVATIVES

[75] Inventors: Fumie Sato, Fujisawa; Takehiro Amano, Tokyo; Kazuya Kameo, Tokyo; Tohru Tanami, Tokyo; Masaru Mutoh, Tokyo; Naoya Ono, Tokyo; Jun Goto, Tokyo, all of Japan

[73] Assignee: Taisho Pharmaceutical Co., Ltd., Japan

[21] Appl. No.: 290,745

[22] PCT Filed: Oct. 18, 1993

[86] PCT No.: PCT/JP93/01493

§ 371 Date: Apr. 19, 1995

§ 102(e) Date: Apr. 19, 1995

[87] PCT Pub. No.: WO94/08959

PCT Pub. Date: Apr. 28, 1994

[30] Foreign Application Priority Data

Oct. 20, 1992 [JP] Japan ..................................... 4-282001

[51] Int. Cl.⁶ ..................... C01C 405/00; A61K 31/557
[52] U.S. Cl. ..................... 514/530; 514/573; 560/118; 562/500
[58] Field of Search ............................ 562/500; 560/118; 514/530, 573

[56] References Cited

U.S. PATENT DOCUMENTS 4,029,681  6/1977  Smith ..................................... 260/408

FOREIGN PATENT DOCUMENTS 0299914  7/1988  European Pat. Off. .
52-100446  8/1977  Japan .
2502009  7/1990  Japan .

OTHER PUBLICATIONS

J. Org. Chem vol. 53, p. 5590 (1988).
Tetrahedron Lett, vol. 30, p. 7083 (1989).
Tsuchida et al, Arzneim–Forsch, vol. 36 p. 1745, 1986.
Handbook of Physiology (Sec. 8 Renal Physiology) p. 103, 1973.

Primary Examiner—Robert Gerstl
Attorney, Agent, or Firm—Lorusso & Loud

[57] ABSTRACT

A prostaglandin derivative represented by formula

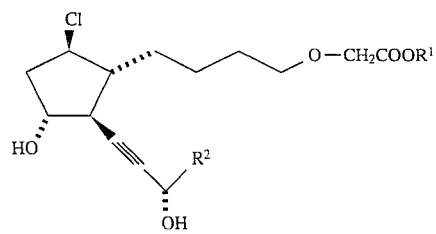

wherein $R^1$ represents a hydrogen atom or a $C_1$–$C_6$ alkyl group, and $R^2$ represents a cyclohexyl group or a cyclopentylmethyl group. This compound has physiological activities such as platelet aggregation-inhibiting action, renal blood vessel and coronary blood vessel-dilating actions and the like, and is useful for treatment of renal failure and diseases of circulatory organs.

6 Claims, No Drawings

PROSTAGLANDIN DERIVATIVES

This application is a 371 of PCT/JP93/01493 filed Oct. 18, 1993.

TECHNICAL FIELD

The present invention relates to novel (9R)-chloro-prostaglandin derivatives.

BACKGROUND ART

Since prostaglandin (hereinafter referred to as PG) shows various important physiological actions in a trace amount, natural PG analogues and a vast number of derivatives thereof have been studied on synthesis and biological activities, with attempt to apply these compounds to pharmaceuticals. The results of the investigations are reported in a number of literature, Japanese Patent Application Kokai (Laid-Open) No. 100446/1977 (U.S. Pat. No. 4,029,681), Japanese Patent Application Kohyo No. 502009/1990 (WO89/00559), etc. Among these publications, Japanese Patent Application Kohyo No. 502009/1990 discloses a group of PG derivatives which are substituted with a halogen at the 9-position; however, the physiological activities of these PG derivatives are not fully satisfactory.

The object of the present invention is to provide novel PG derivatives having strong ameliorating actions for renal failure, ischemic heart disease and heart failure.

DISCLOSURE OF THE INVENTION

The present inventors made a study and found out that particular PG derivatives which have a chlorine atom of R-configuration at the 9-position and a triple bond between the 13-position and 14-position, have excellent physiological activities, particularly ameliorating actions for renal failure, ischemic heart disease and heart failure. The present invention has been completed based on the finding.

According to the present invention there are provided a prostaglandin derivative represented by formula

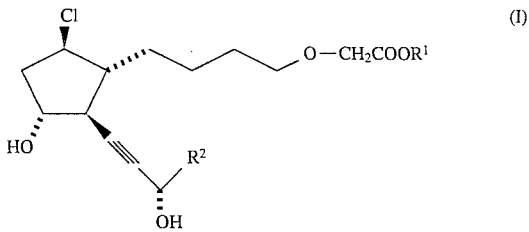

(wherein $R^1$ represents a hydrogen atom or a $C_1$–$C_6$ alkyl group, and $R^2$ represents a cyclohexyl group or a cyclopentylmethyl group), and a salt thereof.

In the present specification, "alkyl group" may be any of a straight chain type and a branched chain type. The $C_1$–$C_6$ alkyl group includes, for example, methyl, ethyl, n-propyl, isopropyl, n-butyl, isobutyl, sec-butyl, tert-butyl, n-pentyl, isopentyl, n-hexyl groups, etc.

The compound of formula (I) wherein $R^1$ represents a hydrogen atom, can be present in the form of a free acid, or in the form of a salt. Examples of such a salt include alkali metal salts such as sodium salt, potassium salt and the like; alkaline earth metal salts such as calcium salt, magnesium salt and the like; other metal salts such as aluminum salt and the like; ammonium salt; salts with organic amines such as trialkylamine (e.g. triethylamine), pyridine and the like. A pharmaceutically acceptable salt is particularly preferable.

The present compound of formula (I) can be produced, for example, by a process summarized in the following reaction scheme A.

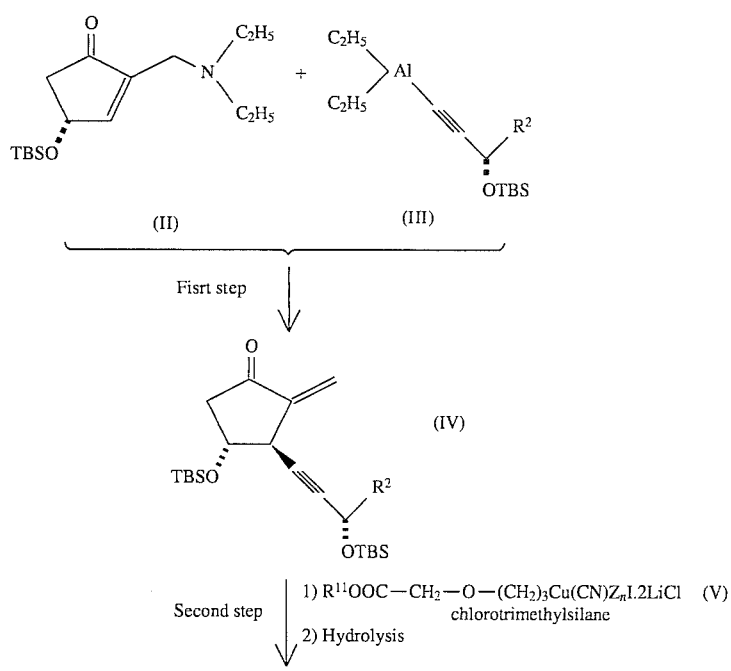

-continued
Reaction Scheme A

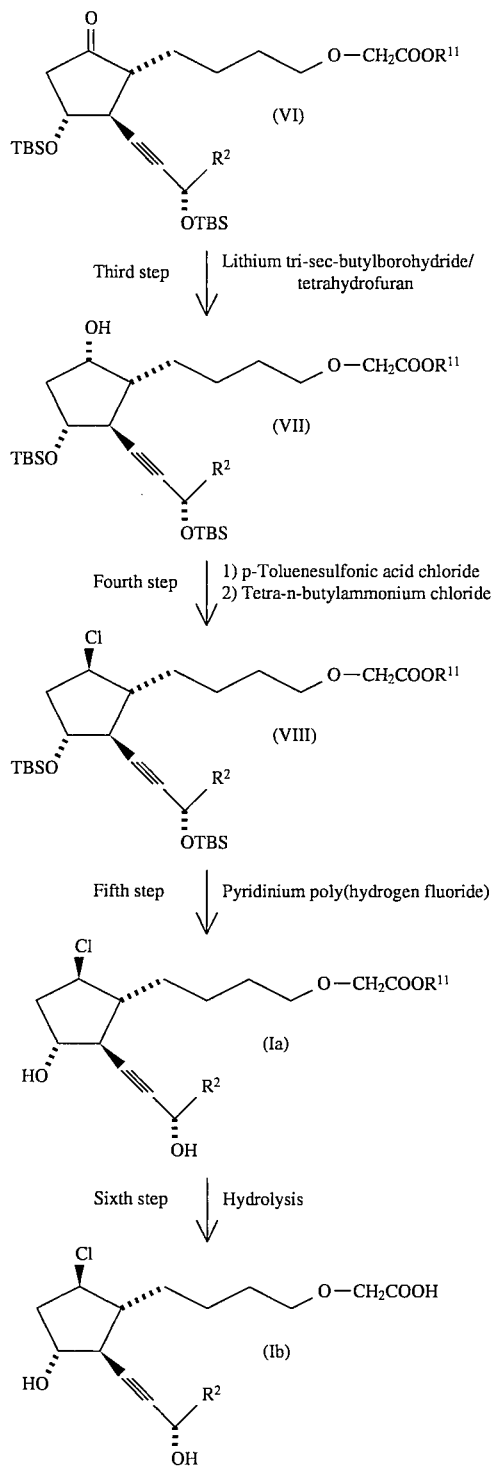

In the above reaction scheme, $R^{11}$ represents a $C_1$–$C_6$ alkyl group; TBS represents a tert-butyldimethylsilyl group; and $R^2$ has the same definition as above.

Each of the first to sixth steps is hereinafter described in more detail.

(First step)

First, a compound of formula (II) known via the process of Sato et al. [J. Org. Chem., Vol. 53, p. 5590 (1988)] is reacted with about 0.8–about 2 equivalents of an organoaluminum compound represented by formula (III) at a temperature of about −10° to about 30° C. in an inert solvent (e.g. toluene, tetrahydrofuran, diethyl ether or the like) to form a compound of formula (IV).

In the above reaction, the organoaluminum compound of formula (III) used as a raw material can be produced, for example, by completely reacting an acetylene compound represented by formula

(IX)

(wherein $R^2$ and TBS have the same definitions as above), produced by the process of Sato et al. [Tetrahedron Lett., Vol. 30, p. 7083 (1989)] with about 0.8–about 1.5 eguivalents of an alkyllithium (e.g. n-butyllithium, tert-butyllithium or the like) in an inert solvent (e.g. toluene, tetrahydrofuran, diethyl ether, n-hexane or the like) at about –20° to about 30° C., preferably about 10° to about 30° C., and then adding about 0.8–about 1.5 equivalents of diethylaluminum chloride at a temperature of about –20° to 30° C.

(Second step)

The compound of formula (IV) obtained in the first step is reacted with about 0.5–4 equivalents of an organocopper compound represented by formula (V) and 0.5–4 equivalents of chlorotrimethylsilane in an inert solvent (e.g. tetrahydrofuran, diethyl ether, methylene chloride, toluene, n-hexane or the like) at a temperature of about –78° C. to about 40° C., and further conducting hydrolysis using an inorganic acid (e.g. an aqueous hydrochloric acid solution) or an organic acid or an amine salt thereof (e.g. p-toluenesulfonic acid, pyridinium p-toluenesulfonate or the like) in an organic solvent (e.g. acetone, methanol, ethanol, isopropanol, diethyl ether, a mixed solvent thereof, or the like) at temperature of about 0° to about 40° C., whereby a compound of formula (VI) can be obtained stereoselectively.

(Third step)

The compound of formula (VI) obtained in the second step is stereoselectively reduced with about 0.8–about 2 equivalents of lithium tri-sec-butylborohydride at about –78° to about 40° C. in an inert solvent (e.g. tetrahydrofuran, diethyl ether, toluene or the like), whereby a compound of formula (VII) can be obtained.

(Fourth step)

The compound of formula (VII) obtained in the third step is reacted with abut 1–about 6 equivalents of p-toluenesulfonic acid chloride in the presence of about 0.8–about 6 equivalents of 4-dimethylaminopyridine in pyridine at about –20° to about 60° C. to give rise to tosylation, and then chlorination is conducted with about 1–about 6 equivalents of tetra-n-butyl ammonium chloride, whereby a compound of formula (VIII) is derived.

(Fifth step)

The compound of formula (VIII) obtained in the fourth step is treated with pyridinium poly(hydrogen fluoride) to remove the protective group (TBS) for hydroxyl group, whereby can be obtained a present compound (Ia)wherein the $R^1$ of formula (I) is a $C_1$–$C_6$ alkyl group.

(Sixth step)

A present compound (Ib) wherein the $R^1$ of formula (I) is a hydrogen atom, can be obtained by hydrolyzing the ester moiety ($R^{11}$) of the compound of formula (Ia) obtained in the fifth step, with about 1–about 6 equivalents of a base (e.g. lithium hydroxide, potassium carbonate or the like) in a solvent ordinarily used in hydrolysis.

Each of the products obtained in the above steps can be, as necessary, separated from the reaction mixture and purified by a per se known method, for example, by chromatography, etc.

The present compound of formula (I), as is clear from the following Test Examples, has a strong inhibitory action for platelet aggregation and a selective, strong and prolonged dilating action for renal blood vessel and coronary blood vessel. When compared with control compound A (the compound described in Example 9 of Japanese Patent Application Kohyo No. 2009/1990), the present compound has a more selective, stronger and more prolonged dilating action for renal blood vessel and a stronger inhibitory action for platelet aggregation. Further, the present compound showed an excellent glomerular filtration-accelerating action and an excellent diuretic action.

TEST EXAMPLE 1

[Test for inhibition of human platelet aggregation]

Blood was collected from human and immediately mixed with a 3.8% aqueous sodium citrate solution in a volume ratio of 9:1. The mixture was centrifuged at 180×g for 15 minutes at room temperature to obtain a platelet-rich plasma (PRP) from the upper layer.

Blood platelet aggregation was determined according to the method of Born [Nature, Vol. 194, p. 927 (1962)].

A mixture of 100 µl of PRP and 5 µl of the drug dissolved in ethanol having various concentrations was incubated with stirring at 37° C. at 1,000 rpm for one minute, and 5 µl of ADP (final concentration: 4.5–12.5 µn) was added to cause aggregation. The maximum aggregation rate induced ADP was evaluated as light transmission using an aggregometer within 5 minutes from the induction of platelet aggregation.

The ratio of the antiaggregation activity was determined by calculating the maximum aggregation obtained when ethanol was used instead of the test drugs. Then the $IC_{50}$ value was calculated from the concentration-response curve of the test compound.

Antiaggregation activity of the test compound was expressed as relative potency against that of $PGE_1$ obtained at the same time.

The results are shown in Table 1.

TABLE 1

| Test compound | Aggregation inhibition activity |
|---|---|
| $PGE_1$ | 1 |
| Control compound* | 9.7 |
| Compound 1** | 40 |
| Compound 2** | 108 |

*Control compound A

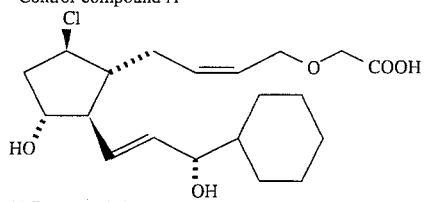

**Compound 1 and compound 2 are compounds of Examples 1 and 2 (described later), respectively.

TEST EXAMPLE 2

[Dilating action for renal blood vessel and blood pressure-lowering action]

Male and female beagles (each weighing 7–11 kg, groups of four) were anesthetized with pentobarbital Na (30 mg/kg i.v.). Their blood pressures were measured by inserting a cannula into each beagle from the femoral artery in a direction counter to blood stream, catching the pressure of the blood flowing through the cannula, with a pressure transducer (TP-400T manufactured by Nihon Kohden Corp.) attached to the cannula, and sending the data of the transducer to a carrier amplifier (AP-630G manufactured by Nihon Kohden Corp.). Their heart rates were measured by recording the arterial wave as trigger pulse by the use of a heart rate counter (AT-600G manufactured by Nihon Kohden Corp.). The left abdomen of each beagle was incised; a probe for electromagnetic flowmeter was fitted to the left renal artery; the probe was connected to an electromagnetic flowmeter (MFV-2100 manufactured by Nihon Kohden Corp.); and there was measured a renal blood flow at the peak of the reaction induced by the administration of each test compound (Tsuchida et al., Arzneim.-Forsch., Vol. 36, p. 1745, 1986). Each compound was dissolved in ethanol and administered into the femoral vein in an amount of 300–3,000 pmol/kg ($PGE_1$), 10–3,000 pmol/kg (control compound A) and 3–1,000 pmol/kg (present compound). The volume administered was 1 μl/kg in each case.

The renal blood flow-increasing action of each test compound was defined as its dose which increased renal blood flow by 15%; the blood pressure-lowering action of each test compound was defined as its dose which lowered blood pressure by 5%; and each of said actions was indicated as a potency ratio when said action of control compound A was taken as 1. The results are shown in Table 2.

TABLE 2

| Test compound | Potency ratio | |
| --- | --- | --- |
| | Renal blood flow-increasing action | Blood pressure-lowering action |
| $PGE_1$ | 0 | 2.0 |
| Control compound A | 1.0 | 1.0 |
| Compound 1 | 3.0 | 4.2 |
| Compound 2 | 3.0 | 2.5 |

TEST EXAMPLE 3

[Glomerular filtration-accelerating action and diuretic action]

(Test method)

Male and female beagles (each weighing 7–10 kg, groups of six) were anesthetized with pentobarbital Na (30 mg/kg i.v.) and then subjected to artificial respiration by laying each beagle on the side. A cannula for measurement of blood pressure, a cannula for test compound administration and continuous injection of creatinine and a cannula for blood collection were inserted into the right brachial artery, right radial skin vein and left saphenous vein of each beagle, respectively. The left abdomen of each beagle was incised and a cannula for urine collection was inserted into the ureter (the blood pressure and heart rate of each beagle were measured in the same manners as in Test Example 2).

The following test was conducted based on the method of Levinsky and Levy [Handbook of Physiology (Section 8; Renal Physiology), p. 103, 1973, American Physiological Society].

At the start of the test, 100 mg/kg of creatinine was administered intravenously. From immediately after the start of the test, a physiological saline solution containing creatinine was continuously injected at a rate of 1 ml/min so that the amount of creatinine injected became 50 mg/kg/hr, whereby the in-blood concentration of creatinine was maintained. After the blood pressure, heart rate, renal blood flow and urine amount became almost stable, urine was collected every 10 minutes with 10 minutes taken as a fraction. In the midst of each fraction, blood was collected to obtain its plasma.

Each test compound was continuously injected into the femoral vein at a solution dose of 5 μl/kg/min by increasing the dose of the test compound continuously at intervals of 10 minutes.

The amount of glomerular filtration was calculated from the following formula.

$GFR$(ml/min)=[(creatinine concentration in urine)×(urine amount)]
/(creatinine concentration in plasma)

Each test compound was prepared by diluting an ethanol solution containing 0.022M of the test compound, with a physiological saline solution so that the dose of the test compound became as follows: when the diluted solution obtained above was administered at a rate of 5 μl/kg/min. Each test compound was injected continuously for 10 minutes at intervals of 10 minutes. The injection rate was 10–300 pmol/kg/min ($PGE_1$), 10–300 pmol/kg/min (control compound A) and 3–300 pmol/kg/min (present compound 1).

(Results)

With $PGE_1$, no increase in renal blood flow, urine amount and amount of glomerular filtration was seen at any dose level. Meanwhile, with control compound A and the present compound, all of the above increases were seen dependently upon the dose. When the potency of increase in renal blood flow, urine amount or amount of glomerular filtration was calculated from the ratio of dose at which said potency was increased by 30%, 20% or 10%, respectively, the present compound 1 showed potencies of 3, 2 and 3 times those of control compound A.

TEST EXAMPLE 4

[Coronary blood vessel-dilating action]

(Test method)

Male and female beagles (each weighing 7–10 kg, groups of six) were anesthetized with pentobarbital Na (30 mg/kg i.v.). A cannula was inserted into each beagle from the femoral artery in a direction counter to blood stream, and the blood pressure was measured by catching the pressure of the blood flowing through the cannula, with a pressure transducer (MPU-0.5 manufactured by Nihon Kohden Corp.) attached to the cannula and sending the data of the transducer to a recorder (WI-681G, WT-685G manufactured by Nihon Kohden Corp.) via a carrier amplifier (AP-620G, AP-621G manufactured by Nihon Kohden Corp.). The heart rate was measured by recording the wave of the femoral artery as a trigger pulse by a heart rate counter (AT-600G manufactured by Nihon Kohden Corp.). The coronary blood flow of each beagle was measured based on the method of Winbury et al. (J. Pharmacol. Exp. Ther., Vol. 168, p. 70, 1969) by subjecting each beagle to thoracotomy, peeling the circumflex of left coronary artery, fitting a probe for blood flow measurement (FR-1.5, 2 manufactured by Nihon Kohden Corp.) to the artery, and connecting the probe to an electromagnetic flowmeter (MFV-2100 manufactured by Nihon Kohden Corp.). The administration of each test compound was made through a cannula inserted into the femoral vein of each beagle. Each test compound was dissolved in ethanol and administered at a proportion (solution) of 1 μl/kg in an amount of 0.3–10 nmol/kg ($PGE_1$), 0.3–1 0 nmol/kg (control compound A) and 0.1–3 nmol/kg (present compound 1). The dilation ratio of coronary blood vessel was expressed as ratio of decrease in coronary blood vessel resistance (coronary blood flow/mean blood pressure), and the potency ratio of test compound was calculated from the ratio of dose of the test compound at which coronary blood vessel resistance was decreased by 20%.

(Results)

The coronary blood vessel resistance-lowering action of control compound A was about 2 times potent than that of $PGE_1$, and the same action of the present compound 1 was about 3 times potent than that of control compound A.

As is clear from the results of the above Test Examples, the present compound has a strong inhibitory action for platelet aggregation, a selective, strong and prolonged dilating action for renal blood vessel and coronary blood vessel, and an excellent glomerular filtration-accelerating action and an excellent diuretic action.

The present compound can, therefore, be used as a drug for treating, for example, various renal failures such as nephritis, nephrosis, renal insufficiency and the like, and diseases of circulatory organs such as ischemic heart disease (angina pectoris), heart failure, hypertension, peripheral circulatory disturbance and the like, all appearing in mammals, particularly in humans.

For this purpose, the compound of the present invention can be made into pharmaceutical preparations suitable for administration, together with pharmaceutically acceptable adjuvants and can be administered orally or parenterally (e.g. intravenously or intrarectally). As the preparation for oral administration, there can be used, for example, solid preparations such as tablets, granules, capsules and the like; and liquid preparations such as solution, fat emulsion, liposome suspension and the like. As the preparation for intravenous administration, there can be used an aqueous or non-aqueous solution, an emulsion, a suspension, a solid preparation which is used by dissolving in a solvent for injection, right before the use, etc. As the preparation for intrarectal administration, there can be used suppositories; and as the preparation for intravaginal administration, there can be used preparations such as pessary and the like.

As the adjuvants used for making such pharmaceutical preparations, there can be cited, for example, excipients such as crystalline cellulose, lactose, corn starch, mannitol and the like; lubricants such as magnesium stearate, talc and the like; binders such as hydroxypropyl cellulose, polyvinylpyrrolidone and the like; disintegrators such as carboxymethyl cellulose calcium and the like; fluidity improvers such as light silicic acid anhydride and the like; dissolving agents such as distilled water for injection, physiological saline solution, Ringer's solution and the like; preservatives such as methyl p-oxybenzoate, propyl p-oxybenzoate and the like; emulsifiers such as gum arabic, lecithin and the like; and surfactants such as Tween, Span and the like.

The present compound can also be made into pharmaceutical preparations by forming an inclusion compound with $\alpha$-, $\beta$- or $\gamma$-cyclodextrin, methylated cyclodextrin or the like.

The dose of the present compound can be varied over a wide range depending upon the age, sex and weight of patient, the condition of disease, the judgement of doctor, etc. However, the daily dose for one ordinary adult is 0.05–60 μg in the case of intravenous or intrarectal administration and 1–600 μg in the case of oral administration, and such a daily dose can be administered in 1–5 portions as necessary.

BEST MODE FOR CARRYING OUT THE INVENTION

The present invention is hereinafter described in more detail by referring to Examples.

In the nomenclature of compound, "nor" in the expression of, for example, "16,17,18,19,20-pentanor" means that there is no carbon chain at the positions (in the above example, there is no carbon chain at the 16–20 positions).

PRODUCTION EXAMPLE 1

(3S)-3-(t-Butyldimethylsiloxy)-3-cyclohexylprop-1-yne (one of the compounds of formula IX)

(1) 25.01 g (0.223 mol) of cyclohexanecarboxaldehyde was dissolved in 150 ml of methylene chloride. Thereto was added 78.24 g (0.234 mol) of methyltriphenylphosphoranilidene acetate. The mixture was stirred at room temperature overnight.

Ethyl acetate was added and the mixture was filtered. The filtrate was concentrated. To the concentrate was added n-hexane. Filtration and concentration were conducted again. The concentrate was subjected to silica gel column chromatography (n-hexane/diethyl ether=95/5) to obtain 31.74 g (0.189 mol) of desired (2E)-3-cyclohexylpropenoic acid methyl ester.

(2) 29.25 g (0.174 mol) of (2E)-3-cyclohexylpropenoic acid methyl ester was dissolved in 200 ml of ether (dried over dry nap). Thereto was added 412 ml (0.383 mol) of diisobutylaluminum hydride (n-hexane solution, 0.93N) in an argon stream at –60° C. over a 15-minute period. The mixture was stirred at the same temperature for 30 minutes. n-Hexane and diethyl ether were added. The resulting mixture was washed with a saturated aqueous ammonium chloride solution, hydrochloric acid (0.2N) and a saturated aqueous sodium chloride solution, dried over magnesium sulfate, and concentrated. The concentrate was purified by silica gel column chromatography (n-hexane/ethyl acetate=19/1 to 9/1) and distillation (57.0°–58.5° C./0.40–0.42 mmHg) to obtain 20.1 g (0.143 mol) of (2E)-3-cyclohexyl-2-propen-1-ol.

(3) To 13.7 g of a white powder (Molecular Sieves of 4Å) were added 210 ml of methylene chloride and 8.60 ml (28.7 mmol) of titanium tetraisopropoxide. The mixture was cooled to –10° to –20° C. Thereto was added 7.30 ml (34.4 mmol) of L(+)-diisopropyl tartarate, and the mixture was stirred for 80 minutes. Thereto was added 68.4 ml of a solution of 20.1 g of (2E)-3-cyclohexyl-2-propen-1-ol in methylene chloride, and the mixture was cooled to –30° C. and stirred for 30 minutes. Thereto was added, over a 50-minute period, 80.6 ml (0.258 mol) of a tert-butylhydroperoxide-methylene chloride solution (3.20N), and the mixture was stirred at –20° C. for 16 hours.

35 ml of dimethyl sulfide was added, and the mixture was stirred for 3 hours. Thereto was added 15.5 ml of 10% tartaric acid, followed by stirring at room temperature for 80 minutes. Sodium fluoride was added, followed by stirring at room temperature for 1 hour. 57.5 g of Celite was added, followed by stirring at room temperature for 30 minutes. Diethyl ether was added, followed by filtration. The filtrate was concentrated.

To the concentrate were added 183 ml of diethyl ether and 115 ml of 1N NaOH. The mixture was stirred for 1 hour and extracted with diethyl ether. The extract was washed with a saturated aqueous sodium chloride solution and concentrated. The concentrate was subjected to silica gel column chromatography (n-hexane/diethyl ether=1/1 to 1/2) to obtain 22.78 g of (2S, 3S)-3-cyolohexyl-2,3-epoxy-1-propanol.

(4) 22.75 g (146 mmol) of (2S,3S)-3-cyclohexyl-2,3-epoxy-1-propanol was dissolved in 230 ml of methylene chloride. Thereto was added 12.4 ml (160 mmol) of mesyl chloride at 0° C. Thereto was dropwise added 24.4 ml (175 mmol) of triethylamine over a 20-minute period. The mixture was stirred at room temperature for 2 hours.

Water was added, followed by extraction with ethyl acetate. The organic layer was washed with hydrochloric acid (1N), a saturated aqueous sodium bicarbonate solution and a saturated aqueous sodium chloride solution in this order, dried over magnesium sulfide, and concentrated to obtain 37.06 g of (1S,2S)-1-cyclohexyl-1,2-epoxy-3-mesyloxypropane.

(5) 37.02 g (158 mmol) of (1S,2S)-1-cyclohexyl-1,2-epoxy-3-mesyloxypropane was dissolved in 260 ml of DMF. Thereto was added 13.4 g (316 mmol) of lithium chloride. The mixture was stirred at 50° C. for 2 hours.

The mixture was concentrated. To the concentrate was added water. The resulting mixture was extracted with n-hexane. The extract was washed with a saturated aqueous sodium chloride solution, dried over magnesium sulfate, and concentrated. The concentrate was subjected to silica gel column chromatography (n-hexane/ethyl acetate=20/1) to obtain 22.56 g of (1S,2R)-3-chloro-1-cyclohexyl-1,2-epoxypropane.

(6) 22.32 g (128 mmol) of (1S,2R)-3-chloro-1-cyclohexyl-1,2-epoxypropane was dissolved in 220 ml of tetrahydrofuran. Thereto was added, at −70° C., 153 ml (383 mmol) of n-butyllithium (n-hexane solution, 2.5N). The mixture was stirred for 1 hour.

A saturated aqueous ammonium chloride solution as added. The mixture was extracted with diethyl ether. The organic layer was washed with 3N hydrochloric acid, a saturated aqueous sodium bicarbonate solution and a saturated aqueous sodium chloride solution in this order, dried over magnesium sulfate, and filtered. The filtrate was concentrated. The concentrate was subjected to silica gel column chromatography (n-hexane/ethyl acetate=6/1 to 3/1) to obtain 18.18 g of (1S)-1-cyclohexyl-2-propyn-1-ol.

(7) 18.10 g (128 mmol) of (1S)-1-cyclohexyl-2-propyn-1-ol was dissolved in 154 ml of DMF. Thereto was added 23.1 g (153 mmol) of tert-butyldimethylsilyl chloride. The mixture was stirred at room temperature for 90 minutes. A saturated aqueous sodium bicarbonate solution was added, and the mixture was extracted with n-hexane. The extract was washed with a saturated aqueous sodium chloride solution, dried over magnesium sulfate, and filtered. The filtrate was concentrated. The concentrate was subjected to silica gel column chromatography (n-hexane/diethyl ether=100/2 to 100/3) and distillation (62.4°–64.2° C./0.45–0.47 mmHg) to obtain 24.77 g (98.1 mmol) of the title compound. b.p.: 62.0°–63.5° C./0.57–0.73 mmHg $^1$H-NMR (CDCl$_3$, 200 MHz) δ ppm: 0.09 (s, 3H), 0.13 (s, 3H), 0.91 (s, 9H), 0.92–1.88 (m, 11H), 2.36 (d, J=2.1 Hz, 1H), 4.09 (dd, J=6.1 Hz, 2.2 Hz, 1H)

IR (neat): 3311, 2929, 2856, 2115, 1473, 1463, 1452, 1386, 1362, 1338, 1252, 1105, 1088, 1069, 1028, 1006, 986, 938, 915, 899, 836, 778, 653, 627, 577 cm$^{-1}$

PRODUCTION EXAMPLE 2

(3S)-3-(t-butyldimethylsiloxy)-4-cyclopentylbut-1-yne

The title compound was produced in the same manner as in Production Example 1. b.p.: 61.0°–62.5° C./0.42–0.48 mmHg $^1$H-NMR (CDCl$_3$, 200 MHz) δ ppm: 0.12 (s, 3H), 0.14 (s, 3H), 0.85–2.09 (m, 11H), 0.91 (s, 9H), 2.37 (d, J=2.0 Hz, 1H), 4.35 (dt, J=6.8 Hz, 2.0 Hz, 1H)

IR (neat): 3312, 2953, 2859, 2114, 1473, 1463, 1386, 1362, 1337, 1253, 1105, 1082, 1006, 940, 838, 810, 778, 654, 627 cm$^{-1}$

EXAMPLE 1

Production of (3-oxa-9-deoxy-9β-chloro-16,17,18,19,20-pentanor-15-cyclohexyl- 13,14-didehydro-PGF$_1$α (compound 1)

(1) (3S)-3-(t-Butyldimethylsiloxy)-3-cyclohexylprop-1-yne (3.61 g) was dissolved in 28.8 ml of benzene. Thereto was added, at 0° C., n-butyllithium (1.95M, hexane solution, 6.4 ml). The mixture was stirred at the same temperature for 30 minutes. Thereto was added, at 0° C., diethylaluminum chloride (0.97M, hexane solution, 14.8 ml), and the mixture was stirred up to room temperature for 30 minutes. Thereto was added, at room temperature, (4R)-2-(N,N-diethylamino)methyl-4-(t-butyldimethyloxy)cyclopent-2-en-1-one (0.25M, benzene solution, 14.8 ml). The mixture was stirred for 15 minutes. The reaction mixture was poured into a hexane (100 ml) — saturated aqueous ammonium chloride solution (100 ml) — aqueous hydrochloric acid solution (3M, 30 ml) mixture with stirring. The organic layer was separated and washed with a saturated aqueous sodium bicarbonate solution (50 ml). The resulting organic layer was dried and concentrated. The residue was purified by silica gel column chromatography (developing solvent: hexane/ether=10/1) to obtain 3.69 g of (3R,4R)-2-methylene-3-[(3'S)-3'-(t-butyldimethylsiloxy)-3'-cyclohexylprop-1'-ynyl]-4-(t-butyldimethylsiloxy)cyclopentan-1-one.

$^1$H-NMR (CDCl$_3$, 200 MHz) δ ppm: 0.07, 0.08 and 0.12 (3s, 12H), 0.88 (s, 18H), 0.92–1.92 (m, 11H), 2.32 (dd, J=7.4 Hz, 17.8 Hz, 1H), 2.71 (dd, J=6.5 Hz, 17.8 Hz, 1H), 3.48–3.58 (m, 1H), 4.11 (dd, J=1.4 Hz, 6.2 Hz, 1H), 4.20–4.32 (m, 1H), 5.55 (d, J=2.6 Hz, 1H), 6.13 (d, J=3.0 Hz, 1H)

IR (neat): 2930, 2850, 1375, 1640, 1470, 1380, 1255, 830, 770 cm$^{-1}$ (2) Copper (I) cyanide.lithium dichloride (1.0M, tetrahydrofuran solution, 9.43 ml, 9.43 mmol) was added to 4-oxo-5-carbomethoxypentylzinc (TT) iodide (0.68M, tetrahydrofuran solution, 11.1 ml, 7.54 mmol) at −60° C. in an argon stream. The mixture was stirred at the same temperature for 15 minutes. Thereto were added, at −60° C., chlorotrimethylsilane (0.86 ml, 6.79 mmol) and solution of the (3R,4R)-2-methylene-3-[(3'S)-3'-(t-butyldimethylsiloxy)-3'-cyclohexylprop- 1'-ynyl]-4-(t-butyldimethylsiloxy)cyclopentan-1-one (1.80 g, 3.77 mmol) obtained in the above (1), in 13.2 ml of diethyl ether. The mixture was heated to 0° C. in about 2 hours with stirring. To the reaction mixture was added 57 ml of a saturated aqueous ammonium chloride solution, followed by extraction with hexane. The organic layer was washed with a saturated aqueous sodium bicarbonate solution and a saturated aqueous sodium chloride solution, dried and concentrated. The residue was dissolved in diethyl ether (3.8 ml) - isopropyl alcohol (15.2 ml). Thereto was added p-toluenesulfonic acid pyridine salt (47 mg, 0.189 mmol). The mixture was stirred at room temperature for 16 hours. To the reaction mixture was added 20 ml of hexane. The mixture was washed with a saturated aqueous sodium carbonate solution and a saturated aqueous sodium chloride solution, dried and concentrated. The residue was purified by silica gel column chromatography (developing solvent: hexane/ethyl acetate=9/1) to obtain 1.42 g of 3-oxa-16,17, 18,19,20 -pentanor-15-cyclohexyl-13,14-didehydro-PGE$_1$ methyl ester 11,15-bis(t-butyldimethylsilyl ether) .

$^1$H-NMR (CDCl$_3$, 200 MHz) δ ppm: 0.08 (s, 3H), 0.09 (s, 3H), 0.10 (s, 3H), 0.12 (s, 3H), 0.82–1.91 (m, 17H), 0.89 (s, 9H), 0.90 (s, 9H), 2.04–2.28 (m, 1H), 2.17 (dd, J=7.0 Hz, 18.2 Hz, 1H), 2.65–2.77 (m, 1H), 2.67 (ddd, J=1.3 Hz, 6.6 Hz, 18.2 Hz, 1H), 3.52 (t, J=6.5 Hz, 2H), 3.76 (s, 3H), 4.05–4.12 (m, 1H), 4.07 (s, 2H), 4.22–4.35 (m, 1 H)

IR (neat): 2930, 2856, 2235, 1747, 147 3, 1463, 1377, 1362, 1253, 1208, 1141, 1102, 1061, 1007, 940, 898, 882,839, 779, 670 cm$^{-1}$ (3) A solution of the compound (1.50 g, 2.46 mmol) obtained in the above (2), tetrahydrofuran (12.3 ml) was cooled to −78° C. The reto was dropwise added lithium tri-sec-butylborohydride (1.0M, tetrahydrofuran solution, 3.20 ml, 3.20 mmol). The mixture was stirred at −78° C. for 1 hour and then returned to room temperature in about 1 hour. Thereto was dropwise added a 35% aqueous hydroperoxide solution (3.2 ml). The mixture was stirred at room temperature for 15 minutes. Thereto were added a saturated aqueous ammonium chloride solution (50 ml) and ether (50 ml). The organic layer was separated, and the aqueous layer was extracted with ether (30 ml). The resulting organic layer was dried using anhydrous magnesium sulfate, followed by filtration. The filtrate was concentrated under reduced pressure to obtain 1.50 g of a crude product of 3-oxa-16,17,18, 19,20 -pentanor-15-cyclohexyl-13,14-didehydro-PGF$_1\alpha$ methyl ester 11,15-bis(t-butyldimethylsilyl ether).

$^1$H-NMR (CDCl$_3$, 300 MHz) δ ppm: 0.08, 0.09, 0.10 and 0.11 (4s, 12H), 0.88 and 0.90 (2s, 18H), 0.92–1.34 (m, 6H), 1.36–1.90 (m, 11H), 1.94–2.06 (m, 2H), 2.42–2.50 (m, 2H), 3.54 (t, J=6.6 Hz, 2H), 3.76 (s, 3H), 4.08 (s, 2H), 4.02–4.10 (m, 1H), 4.10–4.15 (m, 1H), 4.23–4.29 (m, 1H)

IR (neat): 3522, 2931, 2856, 2232, 1757, 1473, 1463, 1451, 1388, 1362, 1255, 1211, 1141, 1104, 1060, 1006, 964, 898, 838, 778, 669 cm$^{-1}$ (4) To a solution of the compound (330 mg, 0.54 mmol) obtained in the above (3), in methylene chloride (1.35 ml) were added 4-dimethylaminopyridine (330 mg, 2.70 mmol) and p-toluenesulfonyl chloride (515 mg, 2.70 mmol). The mixture was heated to room temperature and then stirred for 5 hours. Thereto was added a saturated aqueous sodium hydrogencarbonate solution (15 ml), followed by extraction with hexane. The organic layer was dried using anhydrous magnesium sulfate and then filtered. The filtrate was concentrated under reduced pressure. The resulting crude product was used per se for the following reaction.

To a solution of the crude product (102.3 mg, 0.134 mmol) obtained in the above reaction, in N,N-dimethylformamide (1.0 ml) was added tetra-n-butyammonium chloride (152.7 mg, 0.67 mmol). The mixture was stirred at 40° C. overnight. Thereto was added a saturated aqueous sodium chloride solution (5 ml), followed by extraction with hexane. The organic layer was dried using anhydrous magnesium sulfate and then filtered. The filtrate was concentrated under reduced pressure to obtain 58.3 mg of a crude product of 3-oxa-9 -deoxy-9β-chloro-16,17,18,19,20-pentanor-15-cyclohexyl-13,14 -didehydro-PGF$_1\alpha$ methyl ester 11,15-bis(t-butyldimethylsilyl ether).

$^1$H-NMR (CDCl$_3$, 300 MHz) δ ppm: 0.07, 0.08, 0.09 and 0.10 (4s, 12H), 0.87 and 0.90 (2s, 18H), 0.92–1.30 (m, 6H), 1.38–1.90 (m, 11H), 2.06–2.18 (m, 2H), 2.25–2.32 (m, 2H), 3.53 (t, J=6.6 Hz, 2H), 3.76 (s, 3H), 3.90–4.01 (m, 1H), 4.08 (s, 2H), 4.03–4.10 (m, 1H), 4.20–4.28 (m, 1H)

(5) To a solution of the compound (156.4 mg, 0.236 mmol) obtained in the above (4), in acetonitrile (8 ml) were added, at 0° C., pyridine (0.75 ml) and pyridinium poly (hydrogen fluoride) (0.6 ml). The mixture was stirred for 8 hours with being returned to room temperature. The reaction mixture was poured into ethyl acetate (10 ml)—a saturated aqueous sodium hydrogencarbonate solution (10 ml) with stirring. The aqueous layer was extracted with ethyl acetate. The resulting organic layer was dried using anhydrous magnesium sulfate and then filtered. The filtrate was concentrated under reduced pressure. The resulting crude product was purified by silica gel column chromatography (developing solvent: ethyl acetate/methanol=50/1) to obtain 61.4 mg of 3-oxa-9-deoxy-9β-chloro-16,17,18,19,20 -pentanor-15-cyclohexyl-13,14-didehydro-PGF$_1\alpha$ methyl ester.

$^1$H-NMR (CDCl$_3$, 300 MHz) δ ppm: 0.80–1.35 (m, 6H), 1.40–1.89 (m, 13H), 2.08–2.36 (m, 4H), 3.56 (t, J=6.1 Hz, 2H), 3.76 (s, 3H), 3.90–4.00 (m, 1H), 4.08 (s, 2H), 4.14 (dd, J=1.8 Hz, 6.0 Hz, 1H), 4.31–4.40 (m, 1H)

(6) To a solution of the compound (61.4 mg, 0.142 mmol) obtained in the above (5), in methanol (2.6 ml) and water (0.25 ml) was added lithium hydroxide monohydrate (30 mg, 0.71 mmol). The mixture was stirred at room temperature for 1 hour. Thereto was added ethyl acetate (8 ml). Thereto was added a 0.2N aqueous hydrochloric acid solution in small portions to allow the system to have a pH of 5–6. The aqueous layer was extracted with ethyl acetate. The resulting organic layer was dried using anhydrous magnesium sulfate and then filtered. The filtrate was concentrated under reduced pressure. The resulting crude product was purified by silica gel column chromatography (developing solvent: ethyl acetate/methanol=10/1) to obtain 32.9 mg of 3-oxa-9-deoxy-9β-chloro-16,17,18,19,20-pentanor -15-cyclohexyl-13,14-didehydro-PGF$_1\alpha$.

$^1$H-NMR (CDCl$_3$, 300 MHz) δ ppm: 0.85–1.36 (m, 6H), 1.43–1.90 (m, 13H), 2.08–2.39 (m, 4H), 3.58 (t, J=5.8 Hz, 2H), 3.89 –4.01 (m, 1H), 4.10 (s, 2H), 4.16 (dd, J=1.7 Hz, 5.0 Hz, 1H), 4.30–4.41 (m, 1H)

EXAMPLE 2

Production of 3-oxa-9-deoxy-9β-chloro-17,18,19,20-tetranor -16-cyclopentyl-13,14-didehydro-PGF$_1\alpha$ (compound 2)

The following compounds were produced in steps (1) to (6) in the same manner as in the steps (1) to (6) of Example 1.

(1) (3R,4R)-2-Methylene-3-[(3'S)-3'-(t-butyldimethylsiloxy)-3'-cyclopentylbut- 1'-ynyl]-4-(t-butyldimethylsiloxy)cyclopentan-1-one $^1$H-NMR (CDCl$_3$, 300 MHz) δ ppm: 0.07–0.17 (m, 12H), 0.89 (s, 18H), 1.03–2.02 (m, 11H), 2.33 (dd, J=7.6 Hz, 17.9 Hz, 1H), 2.71 (dd, J=6.4 Hz, 17.9 Hz, 1H), 3.41–3.58 (m, 1H), 4.22–4.31 (m, 1H), 4.39 (t, J=6.7 Hz, 1H), 5.55 (d, J=2.4 Hz, 1H), 6.14 (d, J=3.0 Hz, 1H)

IR (neat): 2930, 2850, 1735, 1638, 1460, 1360, 1245, 1220, 1100, 1000, 935, 825, 770 cm$^{-1}$ (2) 3-Oxa-17,18,19,20-tetranor-16-cyclopentyl-13,14 -didehydro-PGE$_1$ methyl ester 11,15-bis(t-butyldimethylsilyl ether)

$^1$H-NMR (CDCl$_3$, 200 MHz) δ ppm: 0.09 (s, 6H), 0.11 (s, 3H), 0.12 (s, 3H), 0.89 (s, 9 H), 0.90 (s, 9H), 0.95–2.27 (m, 19H), 2.58–2.76 (m, 2H), 3.52 (t, J=6.4 Hz, 2H), 3.76 (s, 3H), 4.07 (s, 2H), 4.22–4.34 (m, 1H), 4.36 (dt, J=6.4 Hz, 1.6 Hz, 1H)

IR (neat): 2953, 2858, 2235, 1747, 1473, 1463, 1439, 1362, 1254, 1208, 1142, 1103, 1006, 940, 839, 779, 670, 577 cm$^{-1}$ (3) 3-Oxa-17,18,19,20-tetranor-16-cyclopentyl-13,14 -didehydro-PGF$_1\alpha$ methyl ester 11, 15-bis(t-butyldimethylsilyl ether)

$^1$H-NMR (CDCl$_3$, 200 MHz) δ ppm: 0.09 (s, 3H), 0.10 (s, 6H), 0.11 (s, 3H), 0.88 (s, 9H), 0.90 (s, 9H), 0.95–2.10 (m, 20H), 2.40–2.51 (m, 1H), 3.55 (t, J=6.4 Hz, 2H), 3.76 (s, 3H), 4.02–4.17 (m, 1H), 4.08 (s, 2H), 4.21–4.30 (m, 1H), 4.36 (dt, J=6.4 Hz, 1.9 Hz, 1H)

IR (neat): 3523, 2952, 2931, 2858, 1758, 1473, 1463, 1439, 1388, 1362, 1253, 1211, 1140, 1103, 1077, 1006, 939, 838, 778, 668 cm$^{-1}$ (4) 3-Oxa-9-deoxy-9β-chloro-17,18,19,20-tetranor-16-cyclopentyl-13,14-didehydro-PGF$_1$α methyl ester 11,15-bis(t-butyldimethylsilyl ether)

$^1$H-NMR (CDCl$_3$, 200 MHz) δ ppm: 0.07 (s, 3H), 0.08 (s, 3H), 0.10 (s, 3H), 0.12 (s, 3H), 0.88 (s, 9H), 0.90 (s, 9H), 0.95–2.17 (m, 20H), 2.28 (ddd, J=8.9 Hz, 5.3 Hz, 1,7 Hz, 1H), 3.54 (t, J=6.5 Hz, 2H), 3.76 (s, 3H), 3.96 (dd, J=15.2 Hz, 7.5 Hz, 1 H), 4.08 (s, 2H), 4.15 (q, J=5.3 Hz, 1H), 4.35 (dt, J=6.5 Hz, 1.7 Hz, 1H)

IR (neat): 2952, 2858, 2233, 1761, 1743, 1472, 1463, 1439, 1389, 1362, 1255, 1206, 1142, 1075, 1006, 940, 838, 812, 778, 670 cm$^{-1}$ (5) 3-Oxa-9-deoxy-9β-chloro-17,18,19,20-tetranor-16-cyclopentyl-13,14-didehydro-PGF$_1$α methyl ester $^1$H-NMR (CDCl$_3$, 300 MHz) δ ppm: 0.83–1.34 (m, 6H), 1.44–1.82 (m, 11H), 1.90 (br. s, 2H), 2.10–2.30 (m, 3H), 2.31 (ddd, J=9.9 Hz, 6.4 Hz, 1.8 Hz, 1H), 3.50–3.60 (m, 2H), 3.76 (s, 3H), 3.95 (dd, J=14.3 Hz, 7.4 Hz, 1H), 4.09 (s, 2H), 4.35 (q, J=6.5 Hz, 1H), 4.42–4.48 (m, 1H)

IR (neat): 3401, 2922, 2852, 2234, 1757, 1447, 1283, 1217, 1140, 1045, 983, 895, 800, 706, 581 cm$^{-1}$ (6) 3-Oxa-9-deoxy-9β-chloro-17,18,19,20-tetranor-16-cyclopentyl-13,14-didehydro-PGF$_1$ α

$^1$H-NMR (CDCl$_3$, 300 MHz) δ ppm: 0.80–2.25 (m, 20H), 2.34 (ddd, J=9.9 Hz, 6.5 Hz, 1,9 Hz, 1H), 2.96 (br. s, 3H), 3.54–3.64 (m, 2H), 3.95 (dd, =13.8 Hz, 7.5 Hz, 1H), 4.10 (s, 2H), 4.36 (q, J=6.5 Hz, 1H), 4.40 (dt, J=7.0 Hz, 1.9 Hz, 1H), IR (neat): 3392, 2945, 2867, 2237, 1732, 1445, 1219, 1134, 1046, 785, 668 cm$^{-1}$

EXAMPLE 3

Production of 3-oxa-9-deoxy-9β-chloro-16,17,18,19,20-pentanor-15-cyclohexyl-13,14-didehydro-PGF$_1$α t-butyl ester (t-butyl ester of compound 1)

The following compounds were produced in steps (2) to (5) in the same manner as in the steps (2) to (5) of Example 1.

(2) 3-Oxa-16,17,18,19,20-pentanor-15-cyclohexyl-13,14-didehydro-PGE$_1$ t-butyl ester 11,15-bis(t-butyldimethylsilyl ether)

$^1$H-NMR (CDCl$_3$, 200 MHz) δ ppm: 0.08 (s, 3H), 0.09 (s, 3H), 0.10 (s, 3H), 0.12 (s, 3H), 0.83–1.93 (m, 17H), 0.89 (s, 9H), 0.90 (s, 9H), 1.48 (s, 9H), 2.09–2.28 (m, 1H), 2.16 (dd, J=18.1 Hz, 7.1 Hz, 1H), 2.65–2.77 (m, 1H), 2.67 (ddd, J=18.1 Hz, 6.5 Hz, 1.4 Hz, 1H), 3.51 (t, J=6.3 Hz, 2H), 3.93 (s, 2H), 4.08 (dd, J=6.2 Hz, 1.5 Hz, 1H), 4.22–4.35 (m, 1H)

IR (neat): 2930, 2857, 2235, 1751, 1473, 1463, 1393, 1369, 1252, 1227, 1136, 1062, 1007, 940, 898, 881, 839, 779, 670, 585 cm$^{-1}$ (3) 3-Oxa-16,17,18,19,20-pentanor-15-cyclohexyl-13,14-didehydro-PGF$_1$ α t-butyl ester 11,15-bis(t-butyldimethylsilyl ether)

$^1$H-NMR (CDCl$_3$, 200 MHz) δ ppm: 0.08 (s, 3H), 0.09 (s,3H), 0.10 (s, 3H), 0.11 (s, 3H), 0.80–1.31 (m, 6H), 0.88 (s, 9H), 0.90 (s, 9H), 1.23 (t, J=7.2 Hz, 2H), 1.38–1.92 (m, 9 H), 1.48 (s, 9H), 1.92–2.05 (m, 2H), 2.41–2.58 (m, 2H), 2.56 (br. s, 1H), 3.53 (t, J=6.4 Hz, 2H), 3.94 (s, 2H), 4.01–4.18 (m, 2H), 4.23–4.30 (m, 1H)

IR (neat): 3523, 2930, 2856, 2231, 1751, 1473, 1463, 1392, 1369, 1251, 1137, 1104, 1059, 1006, 964, 640, 838, 778, 669 cm$^{-1}$ (4) 3-Oxa-9-deoxy-9β-chloro-16,17,18,19,20-pentanor-15-cyclohexyl-13,14-didehydro-PGF$_1$α t-butyl ester 11,15-bis(t-butyldimethylsilyl ether)

$^1$H-NMR (CDCl$_3$, 200 MHz) δ ppm: 0.07 (s, 3H), 0.08 (s, 6H), 0.11 (s, 3H), 0.85–1.32 (m, 6H), 0.87 (s, 9H), 0.90 (s, 9H), 1.26 (t, J=7.2 Hz, 2H), 1.37–1.91 (m, 9H), 1.48 (s, 9H), 2.07–2.17 (m, 3H), 2.29 (ddd, J=8.9 Hz, 4.9 Hz, 1.6 Hz, 1H), 3.52 (t, J=6.5 Hz, 2H), 3.89–4.00 (m, 1H), 3.94 (s, 2H), 4.07 (dd, J=6.2 Hz, 1.6 Hz, 1H), 4.19–4.29 (m, 1 H) , IR (neat): 2931, 2857, 2233, 1750, 1473, 1463, 1392, 1369, 1255, 1137, 1006, 940, 838, 779, 670 cm$^{-1}$ (5) 3-Oxa-9-deoxy-9β-chloro-16,17,18,19,20-pentanor-15-cyclohexyl-13,14-didehydro-PGF$_1$α t-butyl ester $^1$H-NMR (CDCl$_3$, 300 MHz) δ ppm: 0.96–1.34 (m, 6H), 1.26 (t, J=7.1 Hz, 2H), 1.48 (s, 9H), 1.48–1.90 (m, 9H), 1.98 (br. s, 2H), 2.10–2.29 (m, 3H), 2.32 (ddd, J=9.9 Hz, 6.4 Hz, 1.9Hz, 1H), 3.53 (t, J=6.2 Hz, 2H), 3.90–4.00 (m, 1H), 3.95 (s, 2H), 4.14 (dd, ,J=5.9 Hz, 1.7 Hz, 1H), 4.33–4.39 (m, 1H)

IR (neat): 3401, 2978, 2929, 2855, 2234, 1747, 1451, 1394, 1369, 1233, 1161, 1136, 1014, 894, 845, 757 cm$^{-1}$

We claim:

1. A prostaglandin derivative represented by formula

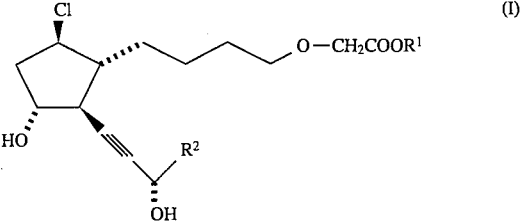

(wherein R$^1$ represents a hydrogen atom or a C$_1$–C$_6$ alkyl group, and R$^2$ represents a cyclohexyl group or a cyclopentylmethyl group), and a salt thereof.

2. A drug containing a compound of formula (I) set forth in claim 1 or a pharmaceutically acceptable salt thereof.

3. An agent for inhibition of platelet aggregation, containing a compound of formula (I) set forth in claim 1 or a pharmaceutically acceptable salt thereof.

4. An agent for treatment of renal failure and diseases of circulatory organs, containing a compound of formula (I) set forth in claim 1 or a pharmaceutically acceptable salt thereof.

5. A pharmaceutical composition containing a compound of formula (I) set forth in claim 1 or a pharmaceutically acceptable salt thereof and pharmaceutically acceptable additives.

6. A method for treatment of renal failure or diseases of circulatory organs in mammals, which comprises administering, to a mammal, an effective amount of a compound of formula (I) set forth in claim 1 or a pharmaceutically acceptable salt thereof.

* * * * *

UNITED STATES PATENT AND TRADEMARK OFFICE
CERTIFICATE OF CORRECTION

PATENT NO. : 5,545,666
DATED     : August 13, 1996
INVENTOR(S) : Sato, et. al.

It is certified that error appears in the above-indentified patent and that said Letters Patent is hereby corrected as shown below:

Col. 6, line 4, "No. 2009/1990" should read --No. 502009/1990--.

Col. 11, line 27, delete "as" insert --was--.

Col. 12, line 36, "(TT)" should read --(II)--.

Col. 13, line 3, "882,839" should read --882, 839--; and
      line 6, "The reto" should read --Thereto--.

Signed and Sealed this

Eighth Day of April, 1997

Attest:

BRUCE LEHMAN

*Attesting Officer*    *Commissioner of Patents and Trademarks*